(12) United States Patent
Poulsen et al.

(10) Patent No.: US 10,849,865 B2
(45) Date of Patent: Dec. 1, 2020

(54) METHOD OF REDUCING NEURONAL CELL DEATH WITH HALOALKYLAMINES

(71) Applicant: THE UNIVERSITY OF MONTANA, Missoula, MT (US)

(72) Inventors: David J. Poulsen, Buffalo, NY (US); Thomas Frederick Rau, Stevensville, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 16/148,825

(22) Filed: Oct. 1, 2018

(65) Prior Publication Data
US 2019/0083423 A1 Mar. 21, 2019

Related U.S. Application Data

(63) Continuation of application No. 14/916,692, filed as application No. PCT/US2014/054569 on Sep. 8, 2014, now abandoned.

(60) Provisional application No. 61/874,865, filed on Sep. 6, 2013.

(51) Int. Cl.
| | |
|---|---|
| *A61K 31/138* | (2006.01) |
| *A61P 25/00* | (2006.01) |
| *A61K 31/137* | (2006.01) |
| *A61K 31/131* | (2006.01) |
| *A61K 9/00* | (2006.01) |

(52) U.S. Cl.
CPC .......... *A61K 31/137* (2013.01); *A61K 9/0019* (2013.01); *A61K 31/131* (2013.01); *A61K 31/138* (2013.01)

(58) Field of Classification Search
CPC .................................................. A61K 31/138
USPC ......................................... 514/651, 654, 655
See application file for complete search history.

(56) References Cited

U.S. PATENT DOCUMENTS

| | | | |
|---|---|---|---|
| 5,513,661 | A | 5/1996 | Hubbard |
| 5,898,035 | A | 4/1999 | Inchiosa et al. |
| 6,009,875 | A | 1/2000 | Hubbard |
| 6,787,553 | B2 | 7/2004 | Adams et al. |
| 9,078,888 | B2 | 7/2015 | Dalton et al. |
| 2004/0063612 | A1 | 4/2004 | Yalpani |
| 2004/0197389 | A1 | 10/2004 | Deagle |
| 2006/0128719 | A1 | 1/2006 | Davidai |
| 2007/0249725 | A1 | 10/2007 | Hubbard |
| 2008/0289438 | A1 | 11/2008 | Bertocci |
| 2009/0197969 | A1 | 8/2009 | Poulsen et al. |
| 2011/0053913 | A1 | 3/2011 | Jhamandas et al. |
| 2011/0105621 | A1 | 5/2011 | Poulsen et al. |
| 2012/0214875 | A1 | 8/2012 | Hughes et al. |
| 2012/0264703 | A1 | 10/2012 | Khan et al. |
| 2013/0266663 | A1 | 10/2013 | Brown et al. |
| 2014/0371322 | A1 | 12/2014 | Glasnapp |
| 2016/0220515 | A1 | 8/2016 | Poulsen et al. |

FOREIGN PATENT DOCUMENTS

| | | |
|---|---|---|
| CA | 2661495 A1 | 2/2008 |
| EP | 0 723 443 | 7/2004 |
| EP | 1476171 | 9/2010 |
| EP | 2466311 | 6/2012 |
| EP | 2106212 | 4/2014 |
| EP | 1476195 | 5/2015 |
| WO | WO 95/10275 | 4/1995 |
| WO | WO 97/07793 | 3/1997 |
| WO | WO 2000/12110 | 3/2000 |
| WO | WO 2002/05851 | 1/2002 |
| WO | WO 2007/057508 | 5/2007 |
| WO | WO 2007/062862 | 6/2007 |
| WO | WO 2008/091555 | 7/2008 |
| WO | WO 2010/148519 | 12/2010 |
| WO | WO 2011/134075 | 11/2011 |
| WO | WO 2012/074561 | 6/2012 |
| WO | WO 2012/080379 | 6/2012 |
| WO | 2012162364 A1 | 11/2012 |
| WO | WO 2012/162364 | 11/2012 |
| WO | WO 2014/201083 | 12/2014 |

OTHER PUBLICATIONS

Adams et al., "Phenoxybenzamine stability in aqueous ethanolic solutions. II Solvent effects upon kinetics", International Journal of Pharmaceutics, 1985, vol. 25, p. 313-327.
Arand et al. "Early inflammatory mediator response following isolated traumatic brain injury and other major trauma in humans" Langenbecks Arch Surg., 2001, vol. 386, pp. 241-248.
Armstrong et al. "The Effects of Alpha Adrenergic Blockade on Arachidonic Acid Metabolism and Shock Sequelae in Endotoxemia", Circulatory Shock, 1986, vol. 20, p. 151-159.
Block et al. "Microglia-mediated neurotoxicity: Uncovering the molecular mechanisms" Nature Reviews | Neuroscience, 2007, vol. 8, pp. 57-69.
Bokesch et al., "The Effects of Phenoxybenzamine on Immediate-Early Gene Expression Aller Hypothermic Circulatory Arrest", Anesthesia & Analgesia, 1998, vol. 86(4S), p. 9SCA.
Brown et al. "Inflammatory Neurodegeneration and Mechanisms of Microglial Killing of Neurons" Mol Neurobiol., 2010, vol. 41, pp. 242-247.
Cimino et al. "Characteristics of the Binding of Phenoxybenzamine to Calmodulin" Biochemical Pharmacology, 1988, vol. 37, No. 14, pp. 2739-2745.
Ghostine et al., "Phenoxybenzamine in the treatment of causalgia", J. Neurosurg., 1984, vol. 60, p. 1263-1268.

(Continued)

*Primary Examiner* — Irina Neagu
(74) *Attorney, Agent, or Firm* — Dinsmore & Shohl LLP (57) ABSTRACT

The present invention is directed to pharmaceutical compositions and methods of treating traumatic brain injury (TBI). The invention is also directed to pharmaceutical compositions and methods of treating a transient hypoxic and/or ischemic condition in the central nervous system. More specifically, the present invention is directed to pharmaceutical compositions and methods of reducing the occurrence of neuronal cell death in the central nervous system, such as, reducing the occurrence brain cell death in the hippocampus and/or the cortex.

10 Claims, 4 Drawing Sheets

(56) References Cited

OTHER PUBLICATIONS

Gustafson et al. Journal of Cerebral Blood Flow and Metabolism 1989, vol. 9, p. 171-174.
Hamill et al. "Catecholamines predict outcome in traumatic brain injury" Annals of Neurology, 1987, vol. 21, No. 5, pp. 438-443.
Hamilton et al. Naunyn-Schmiedeberg's Arch Pharmacol 1984, vol. 325, p. 34-41.
Hamilton et al. "Acute Effects of Phenoxybenzamine on α-Adrenoceptor Responses In Vivo and In Vitro: Relation of In Vivo Pressor Responses to the Number of Specific Adrenoceptor Binding Sites" Journal of Cardiovascular Pharmacology, 1983, vol. 5, No. 5, pp. 868-873.
Inchiosa, Jr Jr., "Phenoxybenzamine in Complex Regional Pain Syndrome: Potential Role and Novel Mechanisms", Anesthesiology Research and Practice, 2013, vol. 201, pp. 1-7.
Inchiosa, Jr. et al., "Treatment of Complex Regional Pain Syndrome Type I with Oral Phenoxybenzamine: Rationale and Case Reports", Pain Practice, 2008, vol. 8.2, p. 125-132.
Janssens et al. "A universal role for MyD88 in TLR/IL-1R-mediated signaling" Trends in Biochemical Sciences, 2002, vol. 27, No. 9, pp. 474-482.
Kenny et al. "Signalling adaptors used by Toll-like receptors: An update" Cytokine, 2008, vol. 43, p. 342-349.
Koegler et al. "Ischemia Contributes to Adverse Effects of Cocaine on Brain Development: Suppression of Ornithine Decarboxylase Activity in Neonatal Rat", Brain Research Bulletin, 1991, vol. 27, pp. 829-834.
Li et al. "Expression of myeloid differentiation primary response protein 88 (Myd88) in the cerebral cortex after experimental traumatic brain injury in rats" Brain Research, 2011, vol. 1396, p. 96-104.
Ling et al. "Expression of intestinal myeloid differentiation primary response protein 88 (Myd88) following experimental traumatic brain injury in a mouse model" Journal of Surgical Research, 2013, vol. 179, p. E227-E234.
McGraw et al., "Cerebral Infection in the Mongolian Gerbil Exacerbated by Phenoxybenzamine Treatment", Stroke, 1976, 7(5), p. 485-488.
Meyer et al., "Cerebral Metabolic Changes During Treatment of Subacute Cerebral Infarction by Alpha and Beta Adrenergic Blockade with Phenoxybenzamine and Propranolol", Stroke, 1974, vol. 5.2, p. 180-195.
Meyer et al., "Influence of Adrenergic Receptor Blockade on Circulatory and Metabolic Effects of Disordered Neurotransmitter Function in Stroke Patients", Stroke, 1976, vol. 7(2), p. 158-167.
Noraberg et al. "Markers for neuronal degeneration in organotypic slice cultures", Brain Research Protocols, 1999, vol. 3, pp. 278-290.
Paul A. Insel "Analgesic-Antipyretic and Antiinflammatory Agents and Drugs Employed in the Treatment of Gout", Goodman & Gilman's The Pharmacological Basis of Therapeutics, Ninth Edition, 1996, pp. 617-655.
Prodjosudjadi et al. "Production and cytokine-mediated regulation of monocyte chemoattractant protein-1 by human proximal tubular epithelial cells" Kidney International, 1995, vol. 48, pp. 1477-1486.
Rau et al. "Treatment with low-dose methamphetamine improves behavioral and cognitive function after severe traumatic brain injury" J Trauma Acute Care Surgery, 2012, vol. 73, No. 2, pp. S165-S172.
Rau et al. "Low dose methamphetamine mediates neuroprotection through a PI3K-AKT pathway" Neuropharmacology, 2011, vol. 61, pp. 677-686.
Rau et al., "Phenoxybenzamine is neuroprotective in a rat model of severe traumatic brain injury", Int. J. Mol. Sci., 2014, vol. 15, p. 1402-1417.
Rhodes et al. "The Temporal Expression, Cellular Localization, and Inhibition of the Chemokines MIP-2 and MCP-1 after Traumatic Brain Injury in the Rat" Journal of Neurotrauma, 2009, vol. 26, pp. 507-525.
Schroeder et al. "Nonfatal Traumatic Brain Injuries from Sports and Recreation Activities," MMWR, 2007, vol. 56, No. 29 pp. 733-737.
Selkirk et al., "Short Communication Over-expression of the human EAAT2 glutamate transporter within neurons of mouse organotypic hippocampal slice cultures leads to increased vulnerability of CA1 pyramidal cells" Europeanu Journal of Neuroscience, 2005, vol. 21, pp. 2291-2296.
Semple et al. "Role of CCL2 (MCP-1) in traumatic brain injury (TBI): evidence from severe TBI patients and CCL2-/- mice" Journal of Cerebral Blood Flow & Metabolism, 2010, vol. 30, p. 769-782.
Strosberg "Structure, function, and regulation of adrenergic receptors" Protein Science, 1993, vol. 2, pp. 1198-1209.
TranT. et al. "Beta blockers exposure and traumatic brain injury: a literature review", Neurosurgery Focus, 2008, vol. 25, No. 4, E8, 6 pages.
Versen et al., "Inhibition of catecholamine uptake in the isolated rat heart by haloalkylamines related to phenoxybenzamine", Br. J. Pharmac., 1972, vol. 46, p. 647-657.
Vest et al. "Effective Post-insult neuroprotection by a Novel $Ca^{2+}$/Calmodulin-dependent Protein Kinase II (CaMKII) inhibitor" The Journal of Biological Chemistry, 2010, vol. 285, No. 27, p. 20675-20682.
Wang Zhongcheng "School references to the clinical diagnosis and treatment of neurosurgical diseases", Peking University Medical Press, 2008, pp. 476-477.
Woolf P. et al. "The predictive value of catecholamines in assessing outcome in traumatic brain injury", Journal of Neurosurgery, 1987, vol. 66, p. 875-882.
Woolf et al. "Free and total catecholamines in critical illness" Am J Physiol. 1988, vol. 254, pp. E287-E291.
Yang et al. "Alterations of Protein Kinase C in Rat Hippocampus Following Traumatic Brain Injury" Journal of Neurotrauma, 1993, vol. 10, No. 3, pp. 287-295.
Zhang et al. "Increased expression of Calcium/Calmodulin-Dependent Protein Kinase Type II Subunit Delta after Rat Traumatic Brain Injury" J Mol Neurosci., 2012, vol. 46, pp. 631-643.
Ziebell et al. "Involvement of Pro- and Anti-inflammatory Cytokines and Chemokines in the Pathophysiology of Traumatic Brain Injury" Neurotherapeutics, 2010, vol. 7, No. 1, pp. 22-30.
"Subunit Delta after Rat Traumatic Brain Injury" J. Mol. Neuroscience, 2012, pp. 631-643, vol. 46.
Search Report dated Jul. 25, 2017, for Chinese Patent Application No. 201480048767.
International Search Report for PCT/US2014/054569 dated Dec. 31, 2014.
Written Opinion of the International Searching Authority for PCT/US2014/054569 dated Dec. 31, 2014.
International Preliminary Report on Patentability for PCT/US2014/054569 dated Aug. 27, 2015.
Rule 71(3) EPC Communication (Intent to Grant) pertaining to corresponding European Patent Application No. 14843058.0, dated Jun. 12, 2020.
Office Action pertaining to corresponding Canadian Patent Application No. 2,923,476, dated Apr. 29, 2020.

METHOD OF REDUCING NEURONAL CELL DEATH WITH HALOALKYLAMINES

CROSS REFERENCE TO RELATED APPLICATIONS

This application is a Continuation of U.S. application Ser. No. 14/916,692, filed Mar. 4, 2016, which is the U.S. National Stage of International Application No. PCT/US2014/054569, filed Sep. 8, 2014, which claims the benefit of U.S. Provisional Patent Application No. 61/874,865, filed Sep. 6, 2013, the contents of each of which are incorporated herein by reference in their entireties.

TECHNICAL FIELD

This application relates to pharmaceutical compositions comprising haloalkylamines, such as, phenoxybenzamine to treat a subject having a traumatic brain injury (TBI) and/or transient hypoxia/ischemia conditions in the central nervous system. Such conditions may lead to oxidative damage, apoptosis, or necrosis in neuronal cells. The disclosed pharmaceutical compositions and methods reduce the occurrence of neuronal cell damage or death resulting from these conditions.

BACKGROUND

Stroke is clinically defined as a rapidly developing syndrome of vascular origin that manifests itself in focal loss of cerebral function. In more severe situations, the loss of cerebral function is global. Stroke can be categorized into two broad types, "ischemic stroke" (about 87%) and "hemorrhagic stroke" (about 10%). Ischemic stroke occurs when the blood supply to the brain is suddenly interrupted. Hemorrhagic stroke happens when a blood vessel located in or around the brain bursts leading to the leakage and accumulation of blood directly in the brain tissue. Additionally, a patient may experience transient ischemic attacks, which indicates a high risk for the future development of a more severe episode. Stroke also includes subarachnoid hemorrhage (about 3%). The symptoms of stroke often include numbness or weakness, especially on one side of the body; sudden confusion or trouble speaking or understanding speech; sudden trouble seeing in one or both eyes; sudden trouble walking; dizziness; or loss of balance or coordination. Despite recent progress understanding stroke mechanisms, stroke management is still not optimal.

Stroke is the third leading cause of death in the world, after only heart disease and cancer. In the United States alone, approximately 780,000 people experience a stroke each year. The cost of stroke in the US is over $43 billion, including both direct and indirect costs. The direct costs account for about 60% of the total amount and include hospital stays, physicians' fees, and rehabilitation. These costs normally reach $15,000/patient in the first three months; however, in approximately 10% of the cases, the costs are in excess of $35,000. Indirect costs account for the remaining portion and include lost productivity of the stroke victim, and lost productivity of family member caregivers (National Institute of Neurological Disorders and Stroke, National Institutes of Health, Bethesda, Md.).

The risk of stroke increases with age. After age 55, the risk of having a stroke doubles every decade, with approximately 40% of individuals in their 80's having strokes. Also, the risk of having a second stroke increases over time. The risk of having a second stroke is 25-40% five years after the first. As the baby boomer generation age, the total number of stroke incidents is projected to increase substantially. And with the over-65 years old portion of the population increasing as the baby boomers reach their golden years, the size of the market for stroke-related therapies will grow substantially. Also, the demand for an effective treatment will increase dramatically.

Traumatic brain injury (TBI) is frequently caused by a sport- or recreation-related injury, and it is a national health concern in the United States. An estimated 1.1 million persons a year, based on CDC and U.S. hospital emergency department statistics, seek hospital treatment for TBI. (CDC: MMWR Weekly. Nonfatal Traumatic Brain Injuries from Sports and Recreation Activities, Jul. 27, 2007; 56(29); 733-737). The highest rates of sports- and recreation-related TBI injuries are associated with males and females between the ages of 10-14 years. TBIs are also common in military situations where brain damage may result from, for example, direct impact, penetrating objects such as bullets and shrapnel, and blast waves caused by explosions.

Acute brain inflammation is most often implicated with a TBI, and the majority of TBIs are categorized as mild. However, even mild TBI can affect a person's ability to return to school or work and can result in long-term cognitive or other problems. In addition, repeated and/or severe TBIs can result in physical, cognitive, behavioral, or emotional problems and lead to various long-term, negative health effects, such as memory loss, behavioral changes, and increased risk for depression. As a result, prevention measures are desirable for TBIs. Of particular concern is the lack of effective treatments to reduce the primary or secondary phase of neuropathology induced by TBI.

The development of novel neuroprotective agents has proven difficult as TBI represents a heterologous injury. While it is clear there are significant differences between stroke and TBI, there are similarities in the mechanisms that lead to neuropathology. Both injuries induce the development of inflammation, reactive oxygen species (ROS), reactive nitrogen species (RNS), excitotoxicity, calcium dysregulation, and apoptosis. TBI also results in sheared blood vessels leading to impaired blood flow and ischemia.

A pressing need exists for a treatment that prevents neuronal damage before it occurs after the occurrence of a transient hypoxic and/or ischemic condition and actually provides neuronal protection. Preventative methods and pharmaceutical compositions are disclosed herein that inhibit or reduce damage and death in neuronal cells before it occurs rather than treating the damage afterwards to promote recovery.

SUMMARY

The present invention relates to the treatment of a transient hypoxic and/or ischemic condition in the central nervous system with a haloalkylamine. In one embodiment, the invention provides a method of treating a transient hypoxic and/or ischemic condition in the central nervous system, the method comprising administering to a subject in need thereof a therapeutically effective amount of a haloalkylamine, such as, phenoxybenzamine or dibenamine. In one aspect, administration of the haloalkylamine reduces the occurrence of neuronal brain cell death, for example in the striatum, hippocampus or the cortex of the subject caused by a transient hypoxic and/or ischemic condition or by a TBI event. In another embodiment, the invention provides a method of reducing the occurrence of neuronal cell death in the central nervous system. The method typically consists of administering to a subject in need thereof a pharmaceutical composition comprising a therapeutically effective amount of a haloalkylamine as at least one of the active ingredients.

The transient hypoxic and/or ischemic condition is often caused by low blood pressure, blood loss, a heart attack, a traumatic brain injury (TBI), a spinal cord injury (SCI), strangulation, surgery, a stroke, a spinal cord infarction, ischemic optic neuropathy, air-way blockage, or neonatal hypoxia or ischemia. The condition, however, can be caused by many conditions, which can be more generally grouped as conditions that cause neuronal cell damage or death in the central nervous system due to the lack of oxygen and/or glucose reaching the neuronal cells for a temporary period of time.

In another embodiment, the invention is directed to a method of treating a transient hypoxic and/or ischemic condition in the central nervous system caused by a TBI event, the method comprising administering to a subject in need thereof a therapeutically effective amount of a haloalkylamine. TBI events include, for example, whiplash, a blast wave impact, and blunt force trauma, wherein the events are of sufficient force to cause neuronal cell damage or death.

In one embodiment, the haloalkylamine is administered as an active ingredient with a pharmaceutically acceptable carrier. The haloalkylamine may be administered with one or more additional active ingredients. The haloalkylamine may also be in an extended release formulation.

In one aspect of the methods of the invention, the haloalkylamine is in unit dosage amounts of about 0.5 mg/kg body weight to about 5, 10, or 20 mg/kg body weight. In another aspect, the haloalkylamine is administered within 24, 18, 16, 14, 12, 10, 8, 6, 4, or 2 hours after onset of the transient hypoxic and/or ischemic condition or the onset of a cause of the condition, for example, the onset of low blood pressure, blood loss, a heart attack, a TBI event, a SCI event, strangulation, surgery, a stroke, a spinal cord infarction, ischemic optic neuropathy, air-way blockage, or neonatal hypoxia or ischemia. The haloalkylamine may be administered via an intravenous injection.

In certain embodiments, the invention relates to a pharmaceutical composition for treating a transient hypoxic and/or ischemic condition in the central nervous system, wherein the composition comprises a haloalkylamine as an active ingredient. In one aspect, the pharmaceutical composition is for treating a transient hypoxic and/or ischemic condition in the central nervous system caused by a TBI event. In another aspect, the pharmaceutical composition reduces the occurrence of neuronal cell death in the subject. For example, the pharmaceutical composition reduces the occurrence of neuronal cell death in neuronal cells of the striatum, hippocampus or the cortex of the subject. In another embodiment, the invention relates to a pharmaceutical composition for reducing the occurrence of neuronal cell death in the central nervous system. In one aspect, neuronal cell death is caused by a transient hypoxic and/or ischemic condition. In another aspect, neuronal cell death is caused by a TBI event.

In one particular embodiment, the haloalkylamine is phenoxybenzamine, dibenamine or a combination thereof. The pharmaceutical composition may comprise haloalkylamine, e.g., phenoxybenzamine, in unit dosage amounts of about 0.5 mg/kg body weight to about 5, 10, 15, or 20 mg/kg body weight. The pharmaceutical composition may further comprise a pharmaceutically acceptable carrier. It may also be in an extended release formulation.

In preferred embodiments, the pharmaceutical composition is administered within 24, 18, 16, 14, 12, 10, 8, 6, 4, or 2 hours after the onset of the transient hypoxic and/or ischemic condition or the onset of a cause of the condition, for example, the onset of low blood pressure, blood loss, a heart attack, a TBI event, a SCI event, strangulation, surgery, a stroke, a spinal cord infarction, ischemic optic neuropathy, air-way blockage, or neonatal hypoxia or ischemia. The pharmaceutical composition is preferably administered via a parenteral or oral route, but other routes are contemplated and can be used depending on the condition.

BRIEF DESCRIPTION OF THE DRAWINGS

FIG. 1G shows neuronal loss presented as relative fluorescence intensity of propidium iodide within the CA1 (black bars), CA3 (white bars) and dentate gyrus (DG-grey bars). OGD=oxygen glucose deprivation exposed cultures; non-OGD=control cultures not exposed to OGD; *** represents $p<0.001$ relative to OGD-exposed cultures.

FIG. 2G shows neuronal loss presented as relative fluorescence intensity of propidium iodide within the CA1 (black bars), CA3 (white bars) and dentate gyrus (DG-grey bars). OGD=oxygen glucose deprivation exposed cultures; non-OGD=control cultures not exposed to OGD; *** represents $p<0.001$ relative to OGD-exposed cultures.

FIG. 3A depicts neurological severity score (NSS), and FIG. 3B depicts foot fault assessments over 30 days after TBI. The dotted lines represent uninjured animals, the diamond-accented lines represent the saline-treated controls, and the circle-accented lines represent the animals treated with 1 mg/kg body weight phenoxybenzamine. * represents $p<0.05$,  represents $p<0.01$, and * represents $p<0.001$, all relative to saline controls.

FIG. 4A shows latency times for rats in the Morris water maze, and FIG. 4B shows the mean time spent in the target quadrant searching for the removed escape platform. Injured saline-treated rats are represented by the square-accented dashed line. Injured phenoxybenzamine-treated rats are represented by the circle-accented dotted line. And sham controls are presented by the diamond-accented solid line. * represents $p<0.05$,  represents $p<0.01$, and * represents $p<0.001$, all relative to saline controls.

DETAILED DESCRIPTION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

The term "haloalkylamine" is used herein to mean haloalkylamine a adrenergic blocking agents, which includes, for example, phenoxybenzamine, dibenamine, and related haloalkylamines and salts thereof.

As used herein, "related haloalkylamines" include, but are not limited to compounds that have structural similarity to phenoxybenzamine and also share some of phenoxybenzamine's adrenergic-related effects. Such compounds are known to persons of skill in the art, e.g., Iversen et al. studied a total of 21 haloalkylamine derivatives, including phenoxybenzamine, for adrenergic-related effects (Iversen L. L. et al., Inhibition of catecholamine uptake in the isolated heart by haloalkylamines related to phenoxybenzamine, Br. J. Pharmac, (1972) 46:647-657; see, e.g., Tables 1 and 2 on pp. 650-651). The chemical cyclization products that are formed spontaneously when phenoxybenzamine or other haloalkylamines are placed in solution are also within the scope of the invention (see, e.g., Adams and Kostenbauder, Phenoxybenzamine stability in aqueous ethanolic solutions. II. Solvent effects on kinetics, International J of Pharmaceutics, (1985) 25:313-327). The disclosure of compounds and their structural formulae in the above two publications is incorporated herein by reference.

As used herein, "neuronal cell death" includes any pathway or mechanism that results in the death of a neuronal cell, e.g., neuronal brain cells or other neuronal cells in the central nervous system. Non-limiting examples of neuronal cell death pathways or mechanisms are apoptosis, necrosis, necroptosis, and excitotoxicity. In certain aspects, the haloalkylamine exerts a neuroprotective effect, for example, by preventing the occurrence of neuronal cell damage or death including reducing the occurrence of oxidative damage, apoptosis, and/or necrosis in neuronal cells in the central nervous system, e.g., neuronal brain cells.

A "salt" refers to salts derived from a variety of organic and inorganic counter ions well known in the art and includes, by way of example only, sodium, potassium, calcium, magnesium, ammonium, and tetraalkylammonium. When the molecule contains a basic functionality, its salt is made with the addition of acid salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth metal ion, or an aluminum ion; or coordinates with an organic base such as ethanolamine, diethanolamine, triethanolamine, trimethylamine, N-methylglucamine, and the like. Salts are suitable for administration in a subject and possess desirable pharmacological properties. Suitable salts further include those described in P. Heinrich Stahl, Camille G. Wermuth (Eds.), Handbook of Pharmaceutical Salts Properties, Selection, and Use; 2002.

As used herein, the terms "non-steroidal anti-inflammatory drug" and "NSAID" include, but are not limited to, those agents which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and-2 aka COX-1 and COX-2), such as the commercially available NSAIDs aceclofenac, acemetacin, acetaminophen, acetaminosalol, acetyl-salicylic acid (aspirin), acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lomoxicam, loxoprofen, meclofenamic acid, mefenamic acid, meloxicam, mesalamine, metiazinic acid, mofezolac, montelukast, mycophenolic acid, nabumetone, naproxen, niflumic acid, nimesulide, olsalazine, oxaceprol, oxaprozin, oxyphenbutazone, paracetamol, parsalmide, perisoxal, phenyl-acethylsalicylate, phenylbutazone, phenylsalicylate, pyrazolac, piroxicam, pirprofen, pranoprofen, protizinic acid, resveratrol, salacetamide, salicylamide, salicylamide-O-acetyl acid, salicylsulphuric acid, salicin, salicylamide, salsalate, sulindac, suprofen, suxibutazone, tamoxifen, tenoxicam, theophylline, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast, rofecoxib and cyclosporine. Additionally, The Merck Manual, 16th Edition, Merck Research Laboratories (1990) pp 1308-1309, as well as The Pharmacological Basis of Therapeutics, 9th edition, Macmillan Publishing Co., 1996, pp 617-655, provide well-known examples of NSAIDs.

The present invention relates to the discovery that haloalkylamines such as phenoxybenzamine may be used to treat transient hypoxia/ischemia conditions in the central nervous system. This treatment reduces the occurrence of neuronal cell damage or death resulting from transient hypoxia/ischemia conditions. The haloalkylamines are unique a adrenergic receptor blocking agents; they form covalent (irreversible) bonds with a adrenergic receptors, thereby causing prolonged blockage of adrenergic transmission to the vasculature of the treated tissue or organ.

Transmission is blocked until there is resynthesis of receptors in the vasculature, which appears to take several days, a week, or more. None of the other currently available a adrenergic receptor antagonists have this property. They act through reversible interactions with the receptors. As a result, their effects diminish as the drug is cleared through systemic circulation (a half-life of 24 hours). Non-limiting examples of haloalkylamines are phenoxybenzamine and dibenamine.

Pharmacologically, phenoxybenzamine (Dibenzyline; Wellspring Pharmaceutical) is a haloalkylamine that blocks both $\alpha$-1 and $\alpha$-2 adrenergic receptors, but has a higher affinity for the $\alpha$-1 receptor. Following intravenous administration, receptor antagonism achieves a peak effect at approximately 1 hour. Phenoxybenzamine exerts a long-term effect in the brain with a half-life of approximately 24 hours. Previous research has shown that reversing the effect of phenoxybenzamine is dependent on the synthesis of new receptors and not the half-life of the drug. Hamilton et al. demonstrated that only 50% of $\alpha$-1 receptors had recovered 8 days after a single administration of phenoxybenzamine (J Cardiovasc Pharmacol (1983) 5(5):868-873). Advantageously, the side effects of phenoxybenzamine are minimal: stuffy nose, mild drowsiness, blurred vision, and upset stomach.

In one embodiment, the present invention is directed to a method of treating a transient hypoxic and/or ischemic condition in the central nervous system by administering to a subject in need thereof a therapeutically effective amount of a haloalkylamine. The haloalkylamine may be phenoxybenzamine, dibenamine, or a related haloalkylamine. As the compound phenoxybenzamine is one of a class of compounds known as haloalkylamine a adrenergic blocking agents, the use of other haloalkylamine a adrenergic blocking agents for the treatment of a transient hypoxic and/or ischemic condition in the central nervous system (CNS) is also within the scope of the present invention.

In certain embodiments, the present invention is directed to methods of reducing the occurrence of neuronal cell damage or death caused by a transient hypoxic and/or ischemic condition by administering to a subject in need of such a treatment a therapeutically effective amount of one of the active agents disclosed herein. In yet other embodiments, the present invention is directed to methods of reducing the occurrence of neuronal cell damage or death caused by transient glucose deprivation by administering to a subject in need of such a treatment a therapeutically effective amount of one of the active agents disclosed herein. Such glucose deprivation may occur in a subject suffering from low blood sugar, for example due to diabetes, endocrine deficiencies, conditions with insulin overproduction, or consumption of certain medications. Such glucose deprivation may also occur locally, for example in ischemic organs and/or cells.

Due to the relationship between neuronal cells and cognition, the present invention in another embodiment relates to methods of improving cognitive function by administering to a subject in need of such a treatment a therapeutically effective amount of one of the active agents disclosed herein. As used herein, "cognitive function" refers to any mental component of brain function. For example, cognitive functions include, but are not limited to, attention, concentration, learning, memory, and focus. Cognition function may also include motor coordination.

The hypoxic and/or ischemic condition treated with the current invention may be caused by any one or more of low blood pressure, blood loss, a heart attack, a traumatic brain injury (TBI), a spinal cord injury (SCI), strangulation, surgery, a stroke, a spinal cord infarction, ischemic optic neuropathy, air-way blockage, or neonatal hypoxia or ischemia. In one embodiment, the invention provides a method of treating a transient hypoxic and/or ischemic condition in the central nervous system caused by a TBI event. Such treatment may reduce the occurrence of neuronal cell damage or death in a subject suffering from TBI. In another embodiment, the invention provides a method of treating a transient hypoxic and/or ischemic condition in the central nervous system caused by a SCI event. Such treatment may reduce the occurrence of neuronal cell damage or death in a subject suffering from SCI.

A TBI as defined herein results from any incident, a TBI event, in which a significant amount of physical force or torsion is applied to the upper torso, neck, or head of an individual, wherein the force is sufficient to cause a transient hypoxic and/or ischemic condition in the brain with the potential to cause neuronal cell damage or death, such as brain cell death. Non-limiting examples of TBI events include a focalized, closed head physical contact; concussive blast wave energy (brain trauma resulting from direct or indirect exposure to an explosion); whiplash events (impact events in which the head has suddenly, forcefully changed direction and velocity); and open wound brain damage in which the skull and dura are penetrated by a foreign object. A TBI event may further be defined as any event in which the individual's normal activity level (basal functioning) is interrupted by an impact event. TBI can be identified by a chart or device showing impact forces for different impact events, e.g., blast, car collision at 30 miles an hour, etc. An example of a device for measuring impact force is a device worn by a soldier (e.g., helmet attachable) or part of a vehicle that can measure the pressure difference cause by a blast wave or blunt force impact, see for example U.S. patent application Ser. No. 12/154,166, entitled "Soft tissue impact assessment device and system," which incorporated by reference herein.

According to the invention, a loss of consciousness is not required in order to find that a subject has suffered a TBI. Significant research into the field of TBIs clearly demonstrates that TBI can cause neuronal cell damage or death even through the subject did not lose consciousness when he or she received the TBI. A subject may be found to have suffered TBI without demonstrating a physical presentation of neurological symptoms depending on the source of the physical force or torsion. For example, a solider subject to concussive blast wave energy in the filed is preferably immediately identified and administered a low dose of the haloalkylamine. Any individual that has been exposed to a significant amount of physical force or torsion applied to the upper torso, neck, or head area would preferably be administered the haloalkylamine in an amount sufficient to reduce the occurrence of neuronal cell damage or death.

As used herein, "spinal cord injury" or "SCI" means an injury in which the axons or nerve fibers of the spinal cord are interrupted. Interruption may be caused by traumatic forces, where the traumatic force fractures, dislocates, crushes or compresses one or more of the vertebrae. Fractures of the vertebrae, can damage the spinal cord from the concussive effect of injury due to displaced bony fragments, or damaged blood vessels, or contusion of emerging nerve roots. Dislocation is often the result of the rupture of an intervertebral disk, and it may result in partial or complete severance of the spinal cord. Penetrating wounds can also cause spinal cord injury when it causes the severance or partial severance of the cord. Traumatic forces may also damage the spinal cord indirectly, for example, damage induced by a blow to the head or a fall on the feet. Aside from the interruption from outside physical forces, bleeding, swelling, inflammation in and around the spinal cord subsequent to damage from traumatic forces may continue the interruption of the axons or nerve fibers of the spinal cord. For example, epidural hemorrhage and spinal subdural hematoma can result in progressive paraparesis due to pressure on the spinal cord.

Spinal cord injury may also be caused without traumatic forces. For example, arthritis, cancer, inflammation, infection, or disk degeneration of the spinal cord results in interruption in the axons and nerve fibers of the spinal cord. Intramedullary injury can be the result of direct pressure on the cord or the passage of a pressure wave through the cord, laceration of the cord by bone, or the rupture of a blood vessel during the passage of a pressure wave through the cord with a hemorrhage into the cord. Intramedullary bleeding and hematoma formation can also be caused by rupture of a weakened blood vessel. Ischemic damage can occur following compression of the anterior spinal artery, pressure on the anastomotic arteries, or damage to major vessels (Gilroy, in Basic Neurology, McGraw-Hill, Inc. New York, N.Y. (1990). Accordingly, non-limiting examples of SCI events are traumatic forces, arthritis, cancer, inflammation, infection, disk degeneration of the spinal cord, intramedullary injury, intramedullary bleeding, or hematoma formation.

Spinal cord injuries can be divided into two categories, complete injuries and incomplete injuries. It is possible that the classification of the injury may change during recovery. Complete spinal cord injuries are usually characterized by the loss of sensation and motor ability and are generally associated with spinal cord injury caused by bruising, loss of blood to the spinal cord, or pressure on the spinal cord. Cut and severed spinal cords are rare. Generally, complete spinal cord injuries result in total loss of sensation and movement below the site of the injury.

Incomplete spinal cord injuries generally do not result in complete loss of movement and sensation below the injury site. A variety of patterns exist to classify such injuries, for example anterior cord syndrome, central cord syndrome, Brown-Sequard syndrome, injuries to individual nerve cells, and spinal contusions. Anterior cord syndrome results from damage to the motor and sensory pathways in the anterior areas of the spinal cord. Effects include loss of movement and overall sensation, although some sensations that travel by way of the still intact pathways can be felt. Central cord syndrome results from injury to the center of the cervical area of the spinal cord. The damage affects the corticospinal tract, which is responsible for carrying signals between the brain and spinal cord to control movement Patients suffering from central cord syndrome experience weakness or paralysis in the arms, and they also experience some loss of sensory reception. The loss of strength and sensation is much less in the legs than in the arms. Many patients with central cord syndrome spontaneously recover motor function, and others experience considerable recovery in the first six weeks following the injury. Brown-Sequard syndrome results from injury to the right or left side of the spinal cord. On the side of the body where the injury occurred, movement and sensation are lost below the level of the injury. On the side opposite the injury, temperature and pain sensation are lost due to the crossing of these pathways in the spinal cord. Injuries to individual nerve cells results in loss of sensory and motor function in the area of the body to which the injured nerve root corresponds. Thus symptoms from these injuries vary depending on the location and function of the particular nerve root affected. Spinal contusions are the most common type of spinal cord injury. In spinal contusion, the spinal cord is bruised, not severed, so the primary consequences are inflammation and bleeding from blood vessels near the injury. A spinal contusion may result in temporary (usually one to two days) incomplete or complete debilitation of the spinal cord or the incomplete or complete debilitation of the spinal cord may be longer term, including a permanent incomplete or complete debilitation of the spinal cord.

In certain embodiments, the disclosed methods further comprise identification of a subject in need of treatment as a result of having suffered from low blood pressure, blood loss, a heart attack, a TBI, a SCI, strangulation, surgery, a stroke, a spinal cord infarction, ischemic optic neuropathy, air-way blockage, or neonatal hypoxia or ischemia. The method may comprise the steps of identifying that a subject has a transient hypoxic/ischemic condition, or a TBI event, and, within 24 hours, 16 hours, 12 hours, 8 hours, 6 hours, 4 hours, or 2 hours of the onset of the condition, administering a haloalkylamine to the subject in an amount sufficient to treat the transient hypoxic and/or ischemic condition or TBI. In some embodiments, the method may comprise the steps of identifying that a subject has a transient hypoxic/ischemic condition and, within 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2 hours, or 1 hour of the onset low blood pressure, blood loss, a heart attack, a TBI event, a SCI event, strangulation, surgery, a stroke, a spinal cord infarction, ischemic optic neuropathy, or air-way blockage, administering a haloalkylamine to the subject in an amount sufficient to treat the transient hypoxic and/or ischemic condition.

Advantageously, the haloalkylamine can be administered after a TBI event or SCI event even prior to the physical manifestation of neurological symptoms of neuronal cell damage or death. Slight to moderate TBI events have even been shown to induce neurological damage that may take months to manifest as physical symptoms. Therefore, in one embodiment, haloalkylamine is administered to a subject as quickly as possible after the TBI event or SCI event. For example, the method may comprises the steps of identifying that a subject suffered a TBI or SCI and, within 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2 hours, or 1 hour of having received the injury, administering a haloalkylamine to the subject in an amount sufficient to treat the transient hypoxic and/or ischemic condition (e.g., to reduce the occurrence of neuronal cell damage or death caused by the TBI or SCI).

The dose regimes disclosed herein are preferably used in this specific TBI and SCI embodiment as well. For example, it is preferable that the step of administering the haloalkylamine to the subject having a TBI event or SCI event comprises one or more intravenous injections of the haloalkylamine. It is also preferable that administration begins as soon as possible after the condition or event.

The methods of the invention advantageously typically reduce the occurrence of neuronal cell damage in the hippocampus, striatum, or cortex of the brain. In certain aspects, the haloalkylamine exerts a neuroprotective effect on neuronal cells by reduction of inflammation, antagonism of the $\alpha$-1 and $\alpha$-2 adrenergic receptors and blocking of norepinephrine signaling, and/or inhibition of calmodulin (CaM)/CaMKII activity. See Example 4. In some aspects, the methods of the invention significantly reduce neurological and cognitive dysfunction.

In certain embodiments, the haloalkylamine is administered along with one or more additional α-blockers. As used herein, an "α-blocker" is an agent that acts as a receptor antagonist of α-adrenergic receptors. An $\alpha_1$-blocker acts against $\alpha_1$-adrenergic receptors, and an $\alpha_2$-blocker acts against $\alpha_2$-adrenergic receptors. In certain aspects, the haloalkylamine is administered with a non-selective α-blocker (e.g., phentolamine, tolazoline, trazodone), an $\alpha_1$-blocker (e.g., alfuzosin, prazosin, doxazosin, tamsulosin, terazosin, silodosin), and/or an $\alpha_2$-blocker (atipamezole, idazoxan, yohimbine).

In some embodiments, the haloalkylamine is administered with one or more anti-inflammatory agents such as a non-steroidal anti-inflammatory drug (NSAID). Such combinations may result in a synergistic neuroprotective effect when administered to a subject suffering from a transient hypoxic and/or ischemic condition in the CNS. In one embodiment, the haloalkylamine is administered with a COX-2 inhibitor. The COX-2 inhibitor may be rofecoxib, celecoxib, cimicoxib, valdecoxib, etoricoxib, parecoxib, lumiracoxib, or diclofenac.

The present invention is also directed to pharmaceutical compositions comprising a haloalkylamine as an active ingredient for the treatment of a transient hypoxic and/or ischemic condition in the central nervous system. The transient hypoxic and/or ischemic condition may be caused by one or more of low blood pressure, blood loss, a heart attack, TBI, SCI, strangulation, surgery, a stroke, a spinal cord infarction, ischemic optic neuropathy, air-way blockage, or neonatal hypoxia or ischemia. In certain embodiments, the pharmaceutical composition comprises a haloalkylamine, an NSAID, and a pharmaceutically acceptable carrier. The NSAID may be a COX-2 inhibitor such as, for example, rofecoxib, celecoxib, cimicoxib, valdecoxib, etoricoxib, parecoxib, lumiracoxib, and diclofenac.

Other pharmaceutical compositions of the present invention comprise a haloalkylamine as an active ingredient for reducing the occurrence of neuronal cell death in the central nervous system. The occurrence of neuronal cell death may be caused by a transient hypoxic and/or ischemic condition. The occurrence of neuronal cell death may also be caused by one or more of low blood pressure, blood loss, a heart attack, a TBI event, a SCI event, strangulation, surgery, a stroke, a spinal cord infarction, ischemic optic neuropathy, air-way blockage, or neonatal hypoxia or ischemia. In certain embodiments, the pharmaceutical composition comprises a haloalkylamine, an NSAID, and a pharmaceutically acceptable carrier. The NSAID may be a COX-2 inhibitor such as, for example, rofecoxib, celecoxib, cimicoxib, valdecoxib, etoricoxib, parecoxib, lumiracoxib, and diclofenac.

Pharmaceutically-acceptable derivatives and salts thereof of phenoxybenzamine and/or related haloalkylamines, and their use for the methods described herein are also within the scope of the present invention. Such salts may be prepared using knowledge in the pharmaceutical arts. Pharmaceutical compositions can be prepared in individual dosage forms. Consequently, pharmaceutical compositions and dosage forms of the invention comprise the active ingredients disclosed herein. The notation of "the pharmaceutical agent" or "neuroprotective agent" signifies the compounds of the invention described herein or salts thereof. Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The invention is preferably administered via a parenteral or oral route, but other routes are contemplated as discussed in detail herein and largely depend on the condition of the subject.

In certain aspects, the active ingredient may be administered in unit dosage amounts of about 0.1 mg/kg body weight to about 20 mg/kg body weight; e.g., any range within about 0.1 mg/kg body weight to about 5, 10, 15, or 20 mg/kg body weight such as 0.2 mg/kg body weight to about 5, 10, or 15 mg/kg body weight, about 0.5 mg/kg body weight to about 7.5 or 10 mg/kg body weight, about 0.5 mg/kg body weight to about 5 mg/kg body weight, about 1 mg/kg body weight to about 5 mg/kg body weight, about 2.5 mg/kg body weight to about 5 mg/kg body weight, etc. In one embodiment, the active ingredient is administered in a unit dosage amount of about 0.5 mg/kg body weight to about 5 mg/kg body weight.

In other aspects, the active ingredient may be administered in a unit dosage amount of less than about 20, 15, or 10 mg/kg body weight, less than about 9 mg/kg body weight, less than about 8 mg/kg body weight, less than about 7 mg/kg body weight, less than about 6 mg/kg body weight, less than about 5 mg/kg body weight, less than about 4 mg/kg body weight, less than about 3 mg/kg body weight, less than about 2 mg/kg body weight, or less than about 1 mg/kg body weight. In one implementation, the active ingredient is administered in a unit dosage amount of less than about 5 mg/kg body weight. In yet other aspects, the active ingredient may be administered in unit dosage amounts of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, or about 100 mg. These unit dosages may be administered once, twice, or three times daily.

In certain embodiments, the active ingredient is administered within 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2 hours, or 1 hour of the onset of the transient hypoxic and/or ischemic condition in the central nervous system. In some embodiments, the active ingredient is administered within 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2 hours, or 1 hour of the onset low blood pressure, blood loss, a heart attack, a TBI event, a SCI event, strangulation, surgery, a stroke, a spinal cord infarction, ischemic optic neuropathy, or air-way blockage. In some aspects, the active ingredient in administered continuously, for example by a continuous IV infusion.

In one embodiment, the active ingredient (e.g., the haloalkylamine) is administered in a pharmaceutical composition comprising a pharmaceutically acceptable carrier. The pharmaceutical composition can be an immediate or extended release formulation depending on the condition and likelihood of reoccurrence. For example, the pharmaceutical composition for treating a transient hypoxic condition may be different than that for treating a transient ischemic condition. Furthermore, the pharmaceutical composition for treating a transient hypoxic and/or ischemic condition may also vary based on the causes for the condition, for example if the condition were caused by strangulation compared to if the condition were caused by stroke.

The composition, shape, and type of dosage forms of the invention will typically vary depending on their route of administration and subject being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art. Frequency of dosage may also vary depending on the compound used and whether an extended release formulation is used. However, for treatment of most disorders, a single dose is preferred.

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, Natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103 and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Parenteral dosage forms can be administered to patients by various routes including, but not limited to, subcutaneous, intravenous, bolus injection, intramuscular, and intraarterial. Preferably the parenteral dosage form is suitable for intravenous delivery. The parenteral dosage forms of the invention are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

For all of the examples provided below, all data was analyzed using Prizm software. To determine Gaussian (normal) distribution a Kolmogorof-Smirnov test was performed on all data sets. Appropriate parametric analysis was performed on data sets containing two groups using an unpaired, one-tailed T-test (CI=95%). Analysis on data sets with more than 2 groups was done using one-way ANOVA with Tukey's post-hoc to determine statistical significance between groups. A $p<0.05$ or less was considered significant.

For experiments requiring TBI, a rat model was used. Male Wistar rats (350-500 g) were obtained from Charles River Laboratories (Wilmington, Mass.) and housed with a 12-hour light/dark cycle and ad libitum access to food and water. Severe TBI was induced using the lateral fluid percussion (LFP) procedure as previously described (Rau et al., 2012, J Trauma and Acute Care Surgery 73:S165). Briefly, a 5 mm trephination was made over the right hemisphere equidistant from the lambda and the bregma. Animals were given a fluid pulse to the brain at 1.9-2.3 atm of pressure for 20 msec. All animals experienced apnea and were manually ventilated until normal breathing occurred. Animals had an average righting time of 24 minutes and a 25% mortality rate was observed. At 8 hours post TBI, phenoxybenzamine (1 mg/kg) was injected into the tail vein of randomly selected rats. Saline treated animals underwent the same tail vein injection procedure receiving only pre-warmed saline. Sham operated animals received a trephination but did not receive a TBI.

Example 1. Phenoxybenzamine Prevents Neuronal Cell Death in Rat Hippocampal Slice Culture-Oxygen Glucose Deprivation Experiments Hippocampal Slice Cultures:

All experimental animal procedures were approved by the University of Montana Institutional Animal Care and Use Committee in accordance with National Institutes of Health guide for the care and use of Laboratory animals (NIH Publications No. 8023). Hippocampal slice cultures were prepared from the brains of 7-day-old Sprague-Dawley rat pups as previously described (Selkirk et al., 2005, Eur J Neur 21:2291). After 7 days in culture, slices were exposed to oxygen-glucose deprivation (OGD). A glucose free balanced salt solution (BSS) composed of 120 mM NaCl, 5 mM KCl, 1.25 mM $NaH_2PO_4$, 2 mM $MgSO_4$, 2 mM $CaCl_2$, 25 mM $NaHCO_3$, 20 mM HEPES, 25 mM sucrose; pH 7.3 was bubbled for one hour with 5% $CO_2$/95% $N_2$ at 10 L/hour. Slices were washed 6 times in deoxygenated SBSS to remove residual glucose, transferred into deoxygenated SBSS, and placed in a 37° C. chamber (Pro-Ox) with an oxygen feedback sensor that maintained gas levels at 0.1% $O_2$, 5% $CO_2$, 94.4% Nitrogen for 60 min. After OGD, the slices were immediately transferred back into pre-warmed Neurobasal media (containing B27 without anti-oxidants) under normal oxygen conditions. Slices treated with phenoxybenzamine in the dose-response study were placed in pre-warmed Neurobasal media containing between 0.1 μM and 1 mM phenoxybenzamine immediately after OGD. For the time course studies, 100 μM phenoxybenzamine was added at 2, 4, 8, or 16 hours after OGD. Neuronal damage was determined by staining slices with propidium iodide (PI; Molecular Probes, Eugene, Oreg.) and quantifying the relative fluorescence intensity (excitation 540/emission 630) using ImagePro Plus software (Media Cybernetics, Silver Springs, Md.). Propidium iodide (P1) was added to the media at a concentration of 2 μM (Noraberg et al., 1999, Brain Research Protocols 3:278), 4 hours prior to OGD. Images were taken of the hippocampal slices prior to OGD to establish baseline fluorescence. After OGD, slices were placed in normal media containing 2 μM PI and imaged again at 24 hours post-OGD using fluorescence optics with an Olympus IMT-2 microscope and a Hamamatsu camera. The total fluorescent intensity in each slice was determined using ImagePro Plus software (Media Cybernetics, Silver Springs, Md.) and all values were expressed as the percent change from untreated slices exposed to OGD.

Results

Figure 1:
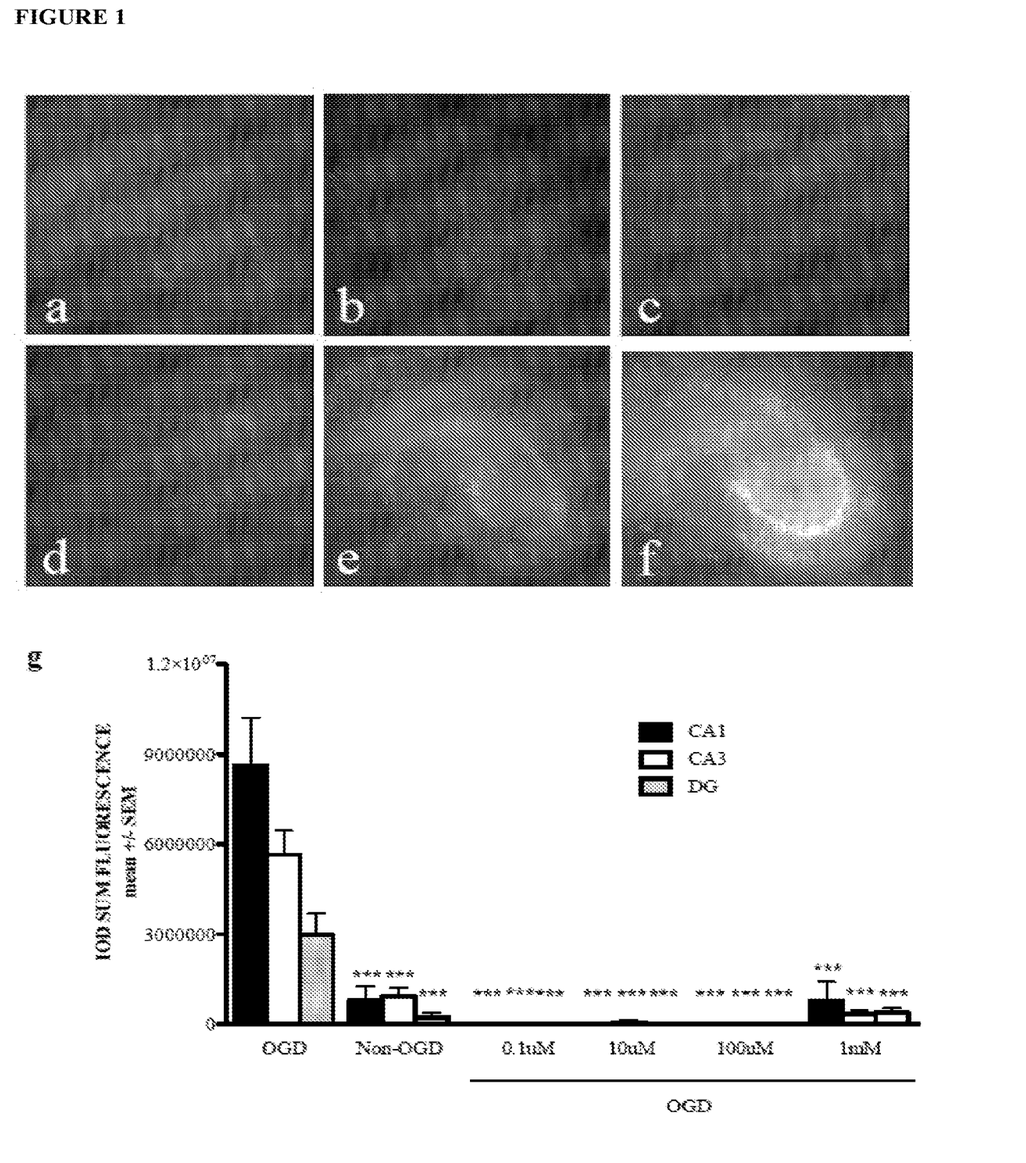
FIG. 1 shows phenoxybenzamine provides significant neuroprotection from oxygen glucose deprivation in rat hippocampal slices cultures. Representative fluorescent images of control slice cultures not exposed to OGD (FIG. 1A) or cultures exposed to OGD then treated with phenoxybenzamine at doses of 0.1 µM (FIG. 1B), 10 µM (FIG. 1C), 100 µM (FIG. 1D), 1 mM (FIG. 1E) or no treatment (FIG. 1F) are shown.
Figure 2:
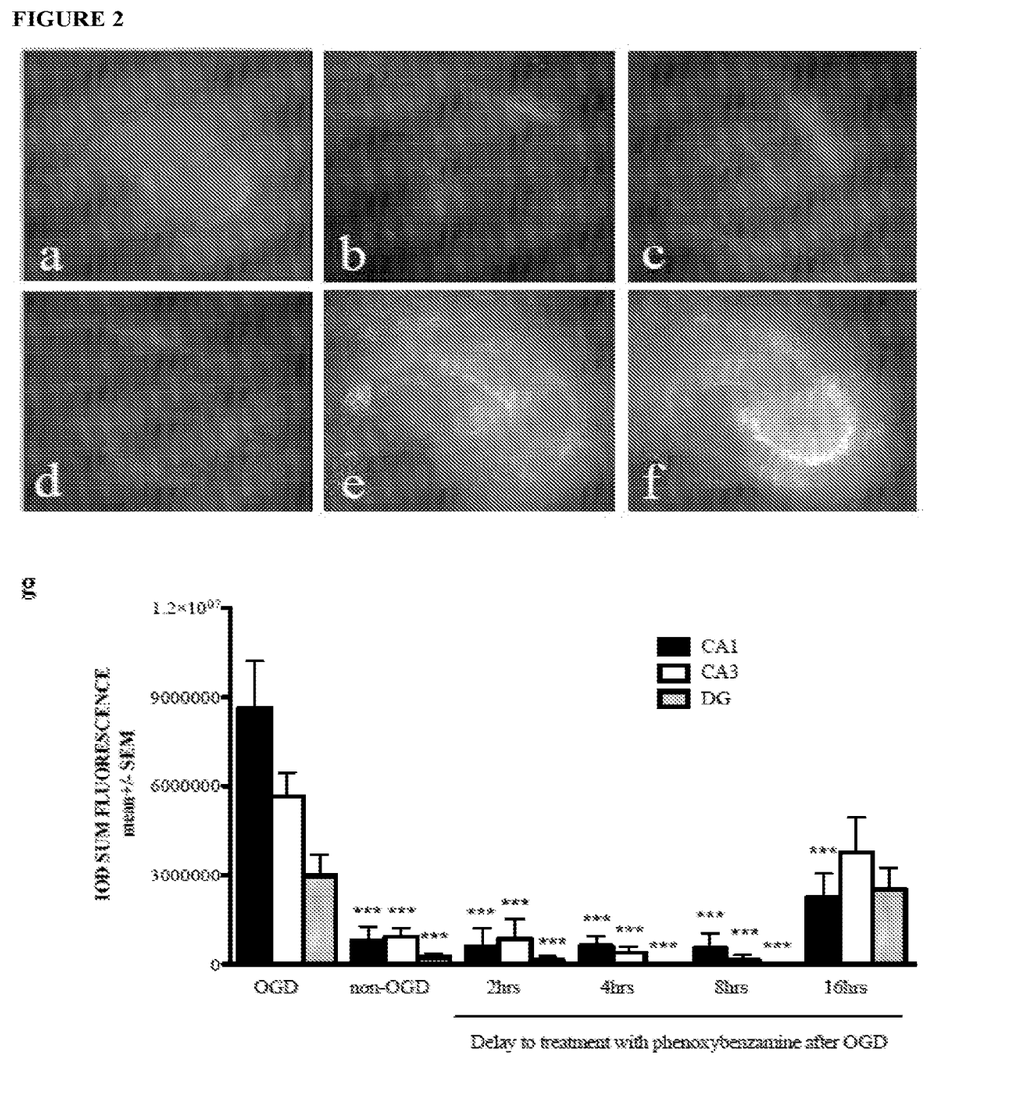
FIG. 2 shows phenoxybenzamine provides significant neuroprotection when delivered up to 16 hours after OGD. Representative fluorescent images of control slice cultures not exposed to OGD (FIG. 2A) or cultures exposed to OGD then treated with phenoxybenzamine at 2 hrs (FIG. 2B), 4 hrs (FIG. 2C), 8 hrs (FIG. 2D), or 16 hrs (FIG. 2E) after OGD or cultures that received no drug treatment (FIG. 2F) are shown.

Our preliminary studies in the rat hippocampal slice culture (RHSC)-OGD model identified phenoxybenzamine as a potential neuroprotective candidate compound. We further tested phenoxybenzamine in the RHSC-OGD model by conducting a dose response study. Phenoxybenzamine preserved primary neurons with in the CA1, CA3 and dentate gyrus and produced a robust neuroprotective effect over a broad dose range (0.1 uM-1 mM final media concentration) (FIG. 1). Neuroprotective compounds must be effective when administered at a clinically relevant time point, which in the case of stroke or traumatic brain injury can be many hours after injury. Therefore, we examined the potential therapeutic window of phenoxybenzamine in the RHSC-OGD model. A middle dose (100 μM) was selected and added to the cultures at 2, 4, 8, or 16 hours post-OGD. We found that phenoxybenzamine prevented neuronal death from OGD in all regions of the hippocampus when delivered at 2, 4, and 8 hours post-OGD. When delivered at 16 hours post-OGD, phenoxybenzamine prevented neuronal death only in the CA1 region of the hippocampus (FIG. 2). These data strongly suggested that phenoxybenzamine might serve as a potential neuroprotective agent.

Example 2. Neurological Severity Scores and Foot Fault Assessments in Phenoxybenzamine Treated TBI Rats are Significantly Better than in the Untreated Controls Neurological Severity Scoring:

Neurological severity scoring (NSS) was performed as previously described (Rau et al., 2011, Neuropharmacology 61:677; Rau et al., 2012 J Trauma and Acute Care Surgery 73:S165). Assessments were conducted on days 1, 7, 14, 21, and 30 by a blinded observer. Animals were scored from 0-16 with 0 indicating no impairment, and 16 indicating maximal impairment. Scoring criteria for a severe TBI was 16-10, a moderate TBI was 9-5 and a mild TBI was 4-1. Animals scoring and NSS of 9 or less on day 1 were identified as having a moderate/mild injury and were excluded.

Foot Faults Assessments:

Foot fault assessments were conducted as previously described (Rau et al., 2011, Neuropharmacology 61:677; Rau et al., 2012 J Trauma and Acute Care Surgery 73:S165). Briefly, rats were set on an elevated grid. With each weight-bearing step, the paw may fall or slip off the wire grid. Each time the left forelimb (affected by damage to the right hemisphere) missed a placement on the wire rack it was recorded as a foot fault. The total number of steps (movement of each forelimb) that the rat used to cross the grid was counted, and the total numbers of foot faults for each forelimb was recorded.

Results

To test the therapeutic potential of phenoxybenzamine, we chose rat lateral fluid percussion injury (LFP) as an in vivo model of severe TBI. We selected the test dose for phenoxybenzamine based on current FDA approved levels. Phenoxybenzamine is usually administered up to 40 mg as much as three times a day (120 mg total). Assuming a typical adult weighs 70 kg, this represents 1.7 mg/kg body weight. Therefore, we selected a slightly lower, single, intravenous dose of 1 mg/kg body weight. This dose was administered at the clinically relevant time point of 8 hours after severe TBI. Therapeutic effectiveness was determined based on behavioral and cognitive outcomes.

Figure 3:
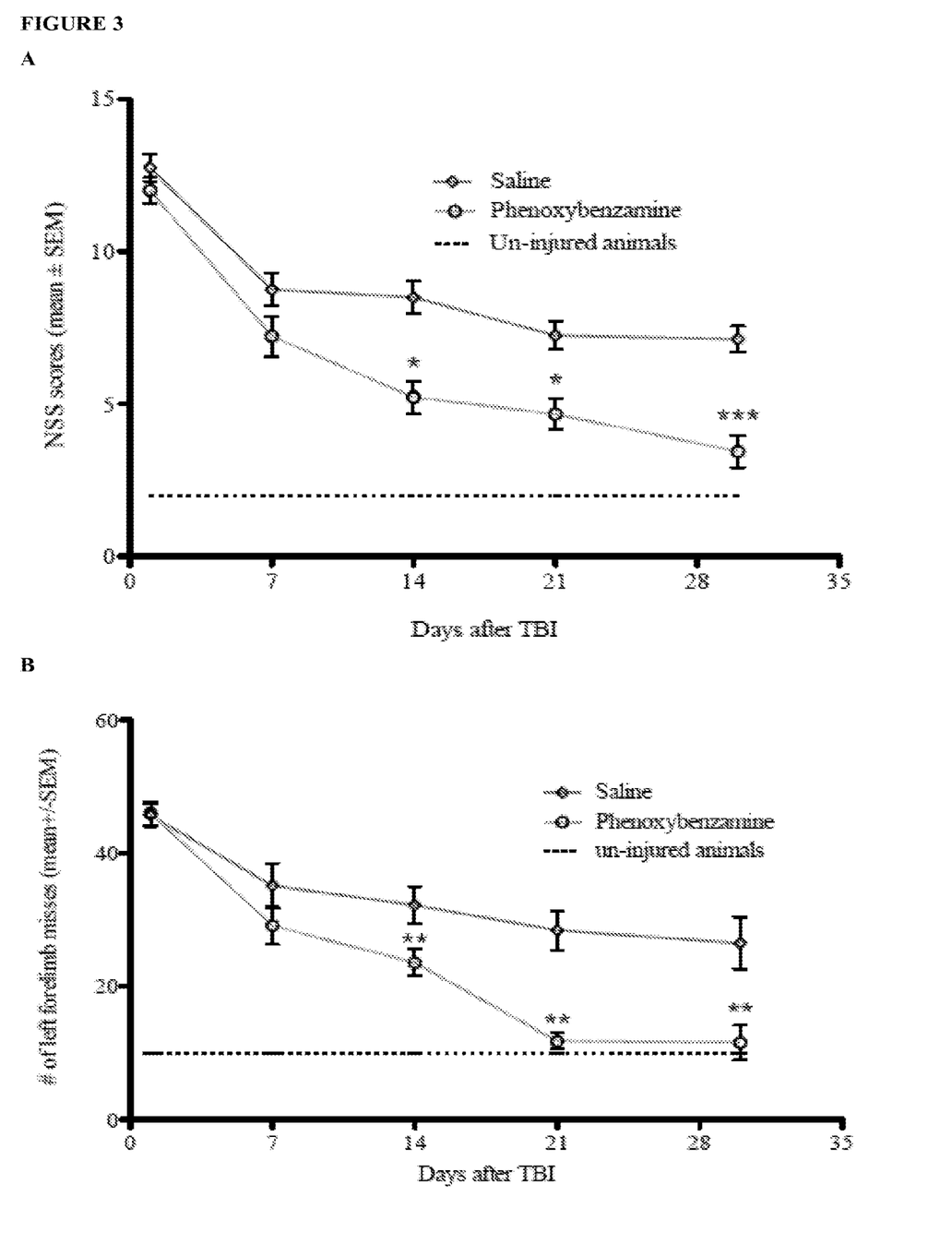
FIG. 3 shows phenoxybenzamine significantly improved behavioral function.

Neurological severity score (NSS) and foot fault assessments were used to test the hypothesis that phenoxybenzamine treatment could improve behavioral outcomes. Animals were assessed 24 hours after injury and again on 7, 14, 21, and 30 days post-TBI. We found no significant differences in NSS or foot fault scoring between the saline and phenoxybenzamine treated animals at 24 hours or 7 days after the TBI. These data indicate that all animals in both treatment groups experienced injuries of similar severity. However, phenoxybenzamine treated animals showed significant improvements in NSS and foot fault scoring on days 14, 21, and 30 (FIG. 3). It is worth noting that phenoxybenzamine treated rats had foot fault values similar to uninjured rats on days 21 and 30 of testing.

Example 3. The Cognitive Function in Phenoxybenzamine Treated TBI Rats is Significantly Better than in the Untreated Controls Assessment of Cognitive Function:

The Morris water maze (MWM) was used to assess the impact of phenoxybenzamine on cognitive function (learning and memory) following TBI. The assessment procedure was performed as previously published (Rau et al., 2011, Neuropharmacology 61:677; Rau et al., 2012 J Trauma and Acute Care Surgery 73:S165). Pre-acclimation began on day 24 post-TBI. The training phase began on day 25 post-injury, and the probe trial was conducted on day 30 post-injury.

Results

Figure 4:
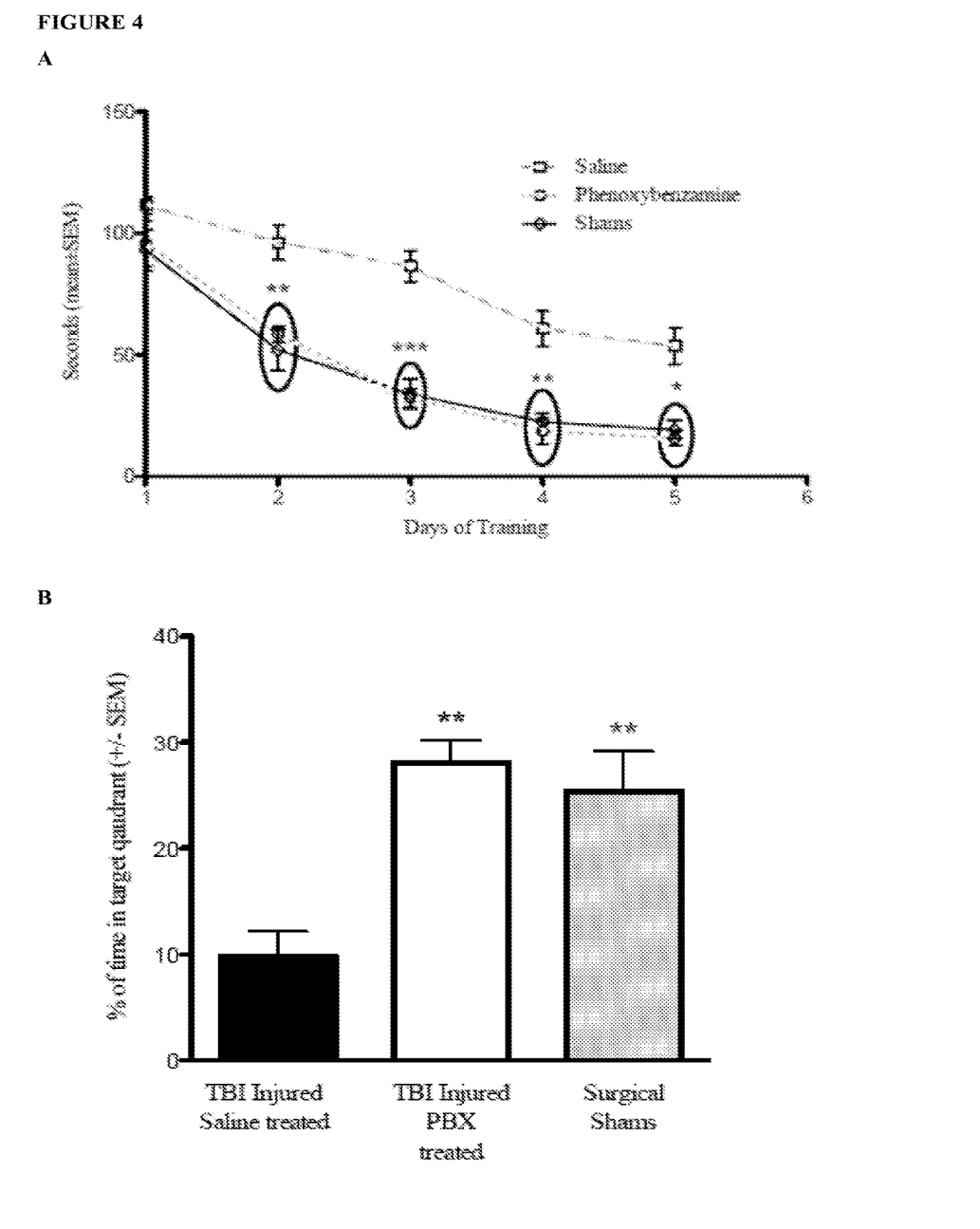
FIG. 4 shows phenoxybenzamine significantly improved learning and memory after severe TBI.

The Morris water maze (MWM) was used to assess cognitive function beginning 25 days after injury. Administration of phenoxybenzamine 8 hours after TBI resulted in a significant improvement in learning on days 2, 3, 4, and 5 of the training phase (FIG. 4A). Surprisingly, phenoxybenzamine treated animals were not significantly different from the un-injured sham control animals on any of the training days. These data suggest that phenoxybenzamine dramatically improves learning after severe TBI. In addition to learning, a probe trial was conducted to assess spatial memory function. During the probe trial the phenoxybenzamine treated animals displayed significantly greater spatial memory capacity than the saline treated controls (FIG.

4B). The phenoxybenzamine treated animals spent approximately 28% of their time searching the target quadrant for the removed escape platform compared to saline treated animals which only 10% of the time in the target quadrant. As in the training phase, the phenoxybenzamine treated TBI injured animals did not differ from un-injured sham controls, which also spent approximately 25% of their time searching the target quadrant (FIG. 4B).

Example 4. Gene Array Analysis Shows Phenoxybenzamine Induces Expression of Pro-Inflammatory Signaling Proteins in Cortical Tissue To elucidate the possible neuroprotective mechanisms involved in phenoxybenzamine-mediated neuroprotection, we performed a gene array analysis of cortical tissue taken from animals 32 hours after the injury (8 hour delay to treatment+24 hours after treatment). This time point was chosen in an effort to detect possible gene changes that would affect the development of secondary damage. We detected a significant increase in the expression of the pro-inflammatory signaling proteins CCL2 (11-fold, p=0.004), IL (4.6-fold, p=0.005) and MyD88 (3-fold, p=0.0001) following severe TBI. In contrast, rats treated with phenoxybenzamine after severe TBI had no significant increase in the expression of these proteins. These data suggest that phenoxybenzamine may mediate neuroprotection by modulating the neuroinflammatory response.

In the current study it has been demonstrated that a single intravenous administration of phenoxybenzamine, delivered 8 hours after TBI, significantly reduced both behavioral and cognitive impairment. This represents a novel finding; there are no previous studies indicating phenoxybenzamine exerts a neuroprotective effect. Currently, phenoxybenzamine is used to treat hypertension and excessive sweating associated with adrenal tumors (pheochromocytoma). Phenoxybenzamine acts as a potent α-1 adrenergic antagonist (with secondary α-2 antagonism) and thus blocks the effects of epinephrine and norepinephrine. There is evidence that suggests blocking the effects of epinephrine and norepinephrine may have a significant benefit to TBI patients. Severe TBI increases the activity of the sympathetic nervous system resulting in the excessive release of epinephrine and norepinephrine (Tran et al., 2008). Previous research indicates a direct correlation between the severity of TBI, plasma epinephrine and norepinephrine levels, and recovery rates (Tran et al., 2008). Patients remaining in a persistent coma have epinephrine and norepinephrine plasma levels severalfold higher than controls. Furthermore, these catecholamine levels remain elevated for the duration of the comatose state. Conversely, TBI patients with initial catecholamine levels that are mildly elevated have been found to consistently improve to a Glasgow Comma Scale (GCS) value greater than 11 at one week post-TBI. In patients with multisystem trauma and TBI, plasma norepinephrine levels at 48 hours post injury are predictive of the GCS at one week, patient survival, the number of ventilator days, and the length of hospital stay, however without TBI, these associations were not present (Woolf 1987, Hamill 1987) (Woolf 1988).

Based on these studies, the neuroprotective effect of phenoxybenzamine may be a direct result of the α-1 and α-2 antagonism that blocks the secondary effects of norepinephrine signaling in the brain. The α-1 adrenergic receptor is coupled to a heterotrimeric G protein, Gq, which activates phospholipase C (PLC) (Strosberg, 1993). PLC produces an increase in IP3 and calcium, which, in turn, activates protein kinase C (PKC) (Strosberg, 1993). Previous studies in TBI have demonstrated that PKC is rapidly elevated as a result of the injury (Yang 1993). Another potential mechanism of neuroprotection associated with phenoxybenzamine is a reduction in calmodulin (CaM)/CaMKII activity. Phenoxybenzamine is a potent inhibitor of CaM/CaMKII activity (Cimino and Weiss, 1988). Under basal conditions CaMKII is a major mediator of glutamate signaling, however, under acute injury conditions, CaM/CaMKII interacts with the NR2B subunit of NMDA receptors leading to excitotoxic death (Vest et al., 2010). There is evidence that CaM/CaMKII increases the trafficking of AMPA receptors to the cell surface leading to greater excitotoxic death during acute injury. Supporting a neurodestructive role for CaMKII, Zhang et al found that TBI increased the expression of CaMKIIδ. Pre-treating rats with a CaMKIIδ inhibitor before TBI resulted in a significant decrease in lesion volume and a significant increase in neuromotor function. Zhang et al went on to elucidate a mechanism in which CaMKIIδ actively promotes apoptosis in neurons by increasing the pro-apoptotic protein BAX and subsequent caspase 3 activation (Zhang et al., 2012).

From gene array studies we found that phenoxybenzamine appears to block critical gene changes that occur after TBI. Genes involved in inflammation such as CCl2, IL-1β, and MyD88 were all significantly elevated in TBI animals, but phenoxybenzamine treated animals did not differ from uninjured controls. This is a crucial finding because inflammation contributes to the formation of edema, a loss of neurons, and negatively affects patient recovery. A key component of brain inflammation is the recruitment of neutrophils and monocytes, which are toxic to neurons (Semple et al., 2010). Recruitment of monocytes into the brain is primarily controlled by monocyte chemotactic protein 1 (MCP-1) otherwise known as CCl2, which is expressed by astrocytes, macrophages, and reactive microglia. After TBI, CCl2 actively recruits monocytes to areas of brain damage leading to inflammation, edema and neuronal damage (Ziebell and Morganti-Kossmann, 2012). Rhodes et al (2009) found a rapid increase in CCl2 in human spinal fluid following severe TBI. Furthermore, CCl2 levels remained significantly elevated for up to 10 days post-injury. Rhodes et al., (2009) also reported that increased levels of CCl2 were detected in the serum of patients who died after TBI.

Epithelial cells actively synthesize CCl2 in response to the proinflammatory cytokine, interleukin-1β (IL-1β) (Prodjosudjadi et al, 1995). From our gene array analysis we found that saline treated animals had a significant increase in IL-1β after TBI whereas phenoxybenzamine treated animals did not have a significant increase. In terms of TBI, IL-1β is the primary activator of microglia and is directly responsible for inducing inflammation. IL-1β further contributes to immunoexcitoxicity by enhancing the sensitivity of NMDA receptors and tumor necrosis factor alpha (TNF-alpha) leading to increased brain inflammation and excitotoxicity (Arand et al., 2001; Block et al., 2007; Brown and Neher, 2010).

Phenoxybenzamine may further reduce post-traumatic inflammation by reducing expression of myeloid differentiation primary response protein 88 (Myd88). Myd88 is a key adaptor protein involved in Toll-like receptor and pro-inflammatory cytokine signal transduction (Li et al., 2011; Ling et al., 2013). In saline treated TBI animals, Myd88 was significantly upregulated over uninjured controls. However, MyD88 expression levels were equivalent to uninjured controls in phenoxybenzamine treated rats after TBI.

Mechanistically, Myd88 is a key adaptor protein for Toll-like receptors, cytokines, and nuclear factor kappaB (NF-κB) (Li et al., 2011; Janssens and Beyaert, 2002). Previous research suggests activation of Toll-like receptors results in the recruitment of Myd88 and the subsequent activation of NF-κB, which in turn, induces the rapid expression of pro-inflammatory molecules including tumor necrosis factor a (TNF-α), IL-1β, interleukin-6 (IL-6), and intracellular adhesion molecule-1 (ICAM-1) leading to a pro-inflammatory response (Janssens and Beyaert, 2002; Kenny and O'Neill, 2008).

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Arand M, Melzner H, Kinzl L, Bruckner U B, Gebhard F. Early inflammatory mediator response following isolated traumatic brain injury and other major trauma in humans. *Langenbecks Arch Surg.* 2001; 386:241-248

Block M L, Zecca L, Hong J S. Microglia-mediated neurotoxicity: Uncovering the molecular mechanisms. *Nat Rev Neurosci.* 2007; 8:57-69

Brown G C, Neher J J. Inflammatory neurodegeneration and mechanisms of microglial killing of neurons. *Mol Neurobiol.* 2010; 41:242-247

Cimino M, Weiss B. Characteristics of the binding of phenoxybenzamine to calmodulin. *Biochem Pharmacol.* 1988; 37:2739-2745

Hamill R W, Woolf P D, McDonald J V, Lee L A, Kelly M. Catecholamines predict outcome in traumatic brain injury. *Ann Neurol.* 1987; 21:438-443

Janssens S, Bcyacrt R. A universal role for myd88 in tlr/il-1r-mediated signaling. *Trends Biochem Sci.* 2002; 27:474-482

Kenny E F, O'Neill L A. Signalling adaptors used by toll-like receptors: An update. *Cytokine.* 2008; 43:342-349

Li G Z, Zhang Y, Zhao J B, Wu G J, Su X F, Hang C H. Expression of myeloid differentiation primary response protein 88 (myd88) in the cerebral cortex after experimental traumatic brain injury in rats. *Brain Res.* 2011; 1396:96-104

Ling H P, Li W, Zhou M L, Tang Y, Chen Z R, Hang C H. Expression of intestinal myeloid differentiation primary response protein 88 (myd88) following experimental traumatic brain injury in a mouse model. *J Surg Res.* 2013; 179:e227-234

Prodjosudjadi W, Gerritsma J S, Klar-Mohamad N, Gerritsen A F, Bruijn J A, Daha M R, van Es L A. Production and cytokine-mediated regulation of monocyte chemoattractant protein-1 by human proximal tubular epithelial cells. *Kidney Int.* 1995; 48:1477-1486

Rhodes J K, Sharkey J, Andrews P J. The temporal expression, cellular localization, and inhibition of the chemokines mip-2 and mcp-1 after traumatic brain injury in the rat. *J Neurotrauma.* 2009; 26:507-525

Semple B D, Bye N, Rancan M, Ziebell J M, Morganti-Kossmann M C. Role of ccl2 (mcp-1) in traumatic brain injury (tbi): Evidence from severe tbi patients and ccl2−/− mice. *J Cereb Blood Flow Metab.* 2010; 30:769-782

Strosberg A D. Structure, function, and regulation of adrenergic receptors. *Protein Sci.* 1993; 2:1198-1209

Tran T Y, Dunne I E, German J W. Beta blockers exposure and traumatic brain injury: A literature review. *Neurosurg Focus.* 2008; 25:E8

Vest R S, O'Leary H, Coultrap S J, Kindy M S, Bayer K U. Effective post-insult neuroprotection by a novel ca(2+)/calmodulin-dependent protein kinase ii (camkii) inhibitor. *J Biol Chem.* 2010; 285:20675-20682

Woolf P D, Hamill R W, Lee L A. Cox C, McDonald J V. The predictive value of catecholamines in assessing outcome in traumatic brain injury. *J Neurosurg.* 1987; 66:875-882

Woolf P D, Hamill R W, Lee L A, McDonald J V. Free and total catecholamines in critical illness. *Am J Physiol.* 1988; 254:E287-291

Yang K, Taft W C, Dixon C E, Todaro C A, Yu R K, Hayes R L. Alterations of protein kinase c in rat hippocampus following traumatic brain injury. *J Neurotrauma.* 1993; 10:287-295

Zhang M, Shan H, Gu Z, Wang D, Wang T, Wang Z, Tao L. Increased expression of calcium/calmodulin-dependent protein kinase type ii subunit delta after rat traumatic brain injury. *J Mol Neurosci.* 2012; 46:631-643

Ziebell J M, Morganti-Kossmann M C. Involvement of pro- and anti-inflammatory cytokines and chemokines in the pathophysiology of traumatic brain injury. *Neurotherapeutics.* 2012; 7:22-30

What is claimed is:

1. A method of treating a traumatic brain injury (TBI) event in a subject, the method comprising administering to the subject a therapeutically effective amount of a pharmaceutical composition comprising phenoxybenzamine or a salt thereof.

2. The method of claim 1, further comprising determining that the subject has had a TBI event and is at risk of neuronal cell death, wherein the TBI event is selected from the group consisting of whiplash, a blast wave impact, and blunt force trauma.

3. The method of claim 1, wherein the pharmaceutical composition comprising phenoxybenzamine or salt thereof is administered in a single dose.

4. The method according to claim 1, wherein the phenoxybenzamine or salt thereof is in unit dosage amounts of about 0.5 mg/kg body weight to about 20 mg/kg body weight.

5. The method according to claim 1, wherein the pharmaceutical composition comprising phenoxybenzamine or salt thereof is administered with a pharmaceutically acceptable carrier.

6. The method according to claim 1, wherein the pharmaceutical composition comprising phenoxybenzamine or a salt thereof is in an extended release formulation.

7. The method according to claim 1, wherein the pharmaceutical composition comprising phenoxybenzamine or a salt thereof is administered within 24 hours after onset of the TBI event.

8. The method according to claim 1, wherein the pharmaceutical composition comprising phenoxybenzamine or a salt thereof is administered within 18 hours after onset of the TBI event.

9. The method according to claim 1, wherein the pharmaceutical composition comprising phenoxybenzamine or a salt thereof is administered in a single dose within 16 hours after onset of the TBI event.

10. The method according to claim 1, wherein the administering is via an intravenous injection.

* * * * *